US00PP29765P3

(12) United States Plant Patent
Lugli et al.

(10) Patent No.: US PP29,765 P3
(45) Date of Patent: Oct. 23, 2018

(54) CHERRY TREE NAMED 'PA7UNIBO'

(50) Latin Name: ***Prunus avium* (L.)L.**
Varietal Denomination: PA7UNIBO

(71) Applicant: ALMA MATER STUDIORUM-UNIVERSITÀ DI BOLOGNA, Bologna (IT)

(72) Inventors: Stefano Lugli, Bologna (IT); Riccardo Correale, Bologna (IT); Michelangelo Grandi, Bologna (IT)

(73) Assignee: ALMA MATER STUDIORUM-UNIVERSITÀ DI BOLOGNA, Bologna (IT)

( * ) Notice: Subject to any disclaimer, the term of this patent is extended or adjusted under 35 U.S.C. 154(b) by 0 days.

(21) Appl. No.: 15/330,889

(22) Filed: Nov. 14, 2016

(65) Prior Publication Data

US 2017/0142880 P1 May 18, 2017

(30) Foreign Application Priority Data

Nov. 12, 2015 (QZ) ..... PBR 2015/2594

(51) Int. Cl.
*A01H 5/08* (2018.01)

(52) U.S. Cl.
USPC ..... Plt./181
CPC ..... *A01H 5/08* (2013.01)

(58) Field of Classification Search
USPC ..... Plt./181
CPC ..... A01H 5/085
See application file for complete search history.

(56) References Cited

U.S. PATENT DOCUMENTS

| | | | |
|---|---|---|---|
| PP25,972 | P3 | 10/2015 | Lugli et al. |
| PP25,981 | P3 | 10/2015 | Lugli et al. |
| PP25,982 | P3 | 10/2015 | Lugli et al. |
| PP25,997 | P3 | 10/2015 | Lugli et al. |
| 2017/0118881 | P1 | 4/2017 | Lugli et al. |

*Primary Examiner* — Kent L Bell
(74) *Attorney, Agent, or Firm* — Arent Fox LLP

(57) ABSTRACT

Variety Denomination 'PA7UNIBO' is a novel cherry tree derived from a seedling of unknown cross which was planted at Vignola, Modena Province, Italy. The genus and species (cultivar) of 'PA7UNIBO' is *Prunus avium*. It was initially propagated by grafting to root stocks of varying vigor and, after testing in districts and plantings of differing types, proved to have qualities for a promising new cultivar for the market.

5 Drawing Sheets

Latin name and variety denomination: Latin name of the genus/species of the plant claimed (cultivar): *Prunus avium* (L.)L.

Variety denomination: 'PA7UNIBO'.

CROSS-REFERENCE TO RELATED APPLICATIONS

This application claims priority under 35 U.S.C. § 119 to CPVO (Community Plant Variety Office) Application No. 201502594, titled, 'PA7UNIBO', which was filed on Nov. 12, 2015, which is hereby incorporated herein by reference in its entirety.

The European Trademark for 'Sweet Stephany' was registered on Aug. 1, 2016 as Registration No. 014997911. This European Trademark is associated to 'PA7UNIBO', and used to distinguish such cherry variety from others.

BACKGROUND OF INVENTION

*Prunus avium* 'PA7UNIBO ' originally derived from as seedling. The seedling is of unknown parentage and was selected in 2004 in Vignola, Modena, Province, Italy. The seedling was named and tested as DCA BO B5 A89. The seedling was initially propagated by grafting. Grafting was done on different rootstocks of varying vigor, and tested in different growing districts and planting densities. These studies demonstrated that the new selection has properties for a new cultivar for the market. The harvest is in the third to fourth week of June in Modena, Province, more precisely, about 27-28 days after 'Burlat' and approximately 6-9 days after 'Bing'.

BRIEF SUMMARY OF INVENTION

The name of a closest comparison cultivar 'PA7UNIBO' is 'Lapins'. 'Lapins' has an approximate harvest date comparable to 'PA7UNIBO' (e.g., 'Lapins' ripens approximately 6-8 days after 'Bing'), however, compared to 'Lapins', PA7UNIBO's fruit is larger, comparable in size to 'Duroni 3' and 'Sunburst' varieties (with an average caliber of between 30 and 32 mm). 'PA7UNIBO' was selected for specific quality features, including tree growth and yield performance (similar to 'Lapins'), fruit appearance (medium red, comparable to 'Lapins'), unusual taste-flavor properties attributed the unique sugar content and acidity ratios, which are higher than 'Lapins'. The color of flesh is medium red (comparable to 'Lapins'). The fruit is firmer than 'Lapins'. Other distinctive traits of 'PA7UNIBO' also include mid-to-late picking date, in the third to fourth week of June in Modena Province, approximately 27-28 days after 'Burlat' and approximately 6-9 days after 'Bing'.

The date of cross was in the year 2000. The location of the discovery was Vignola, Modena Province, Italy. The date of the first asexual propagation was in 2008 in Vignola, Modena Province, Italy. 'PA7UNIBO' resulted from a cross of unknown varieties, but was initially propagated on root stock of 'Gisela 6' in the trial fields to test field and cropping performance in a medium-to-high density planting.

BRIEF DESCRIPTION OF THE FIGURES

The accompanying photographs show typical specimens of the new variety as depicted in color as nearly true as is reasonably possible in color illustrations of this character.

DETAILED BOTANICAL DESCRIPTION OF 'PA7UNIBO'

Figure 1:
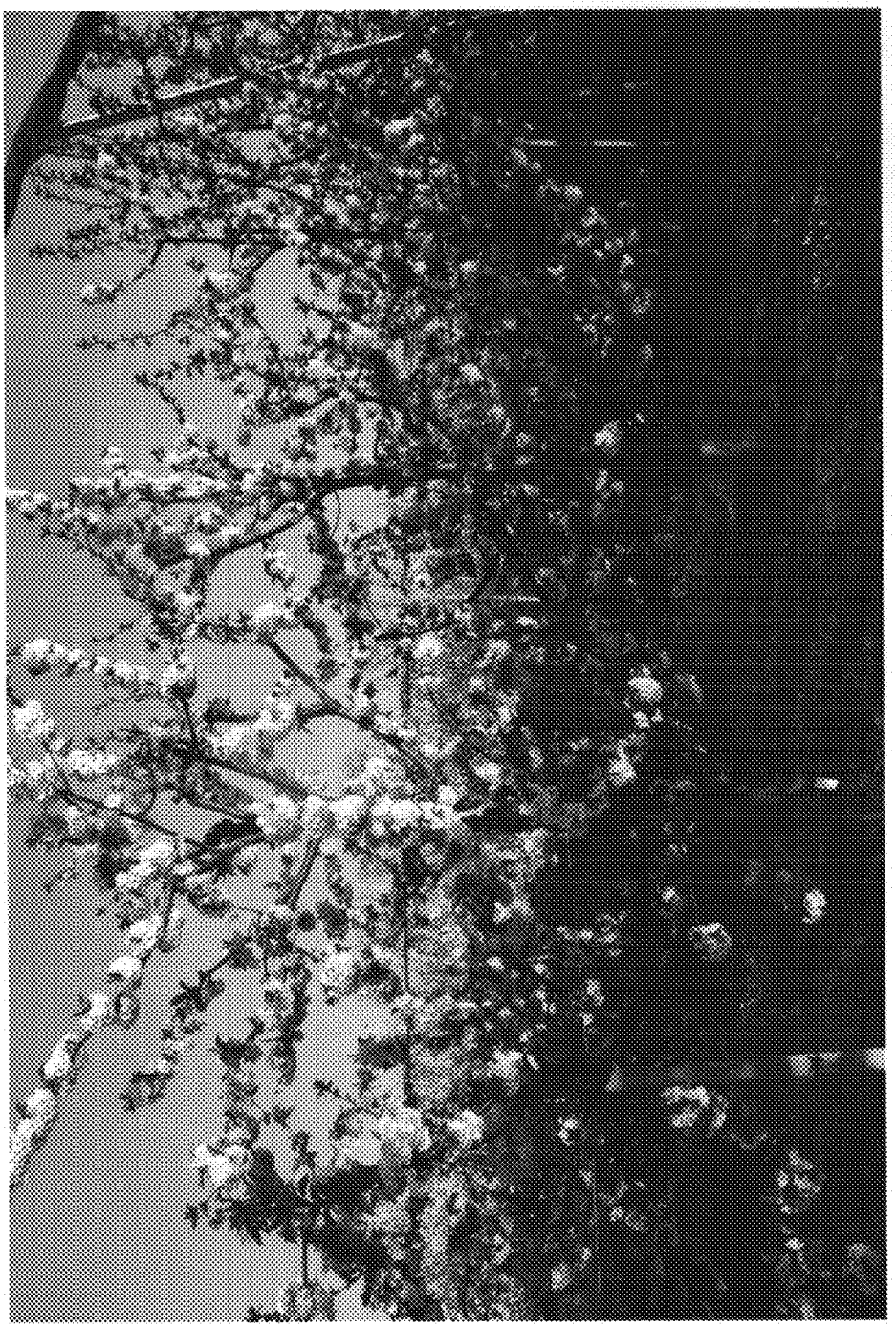
FIG. 1 illustrates trees of 'PA7UNIBO' at blooming time.
Figure 2:
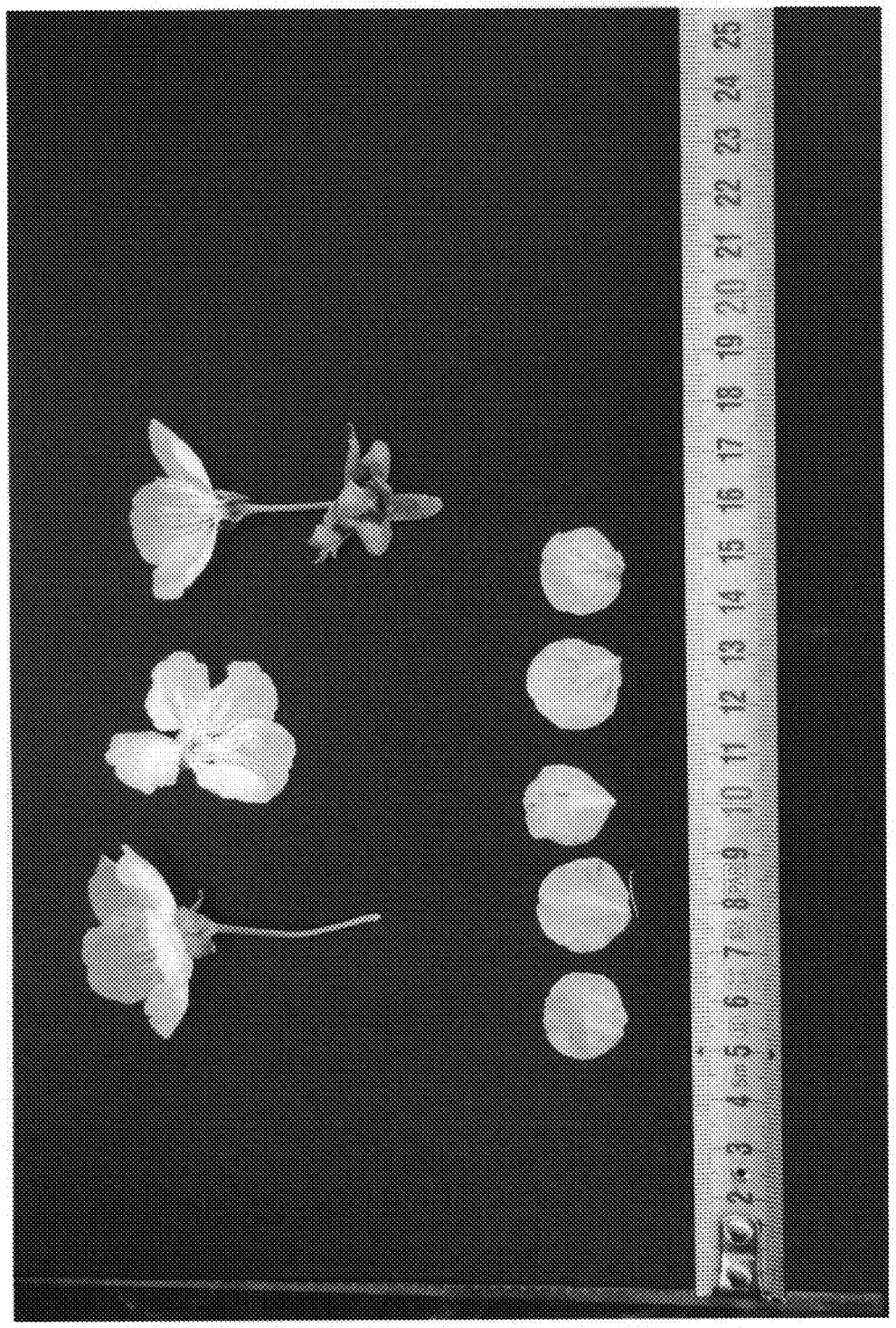
FIG. 2 shows the flowers of 'PA7UNIBO'.
Figure 3:
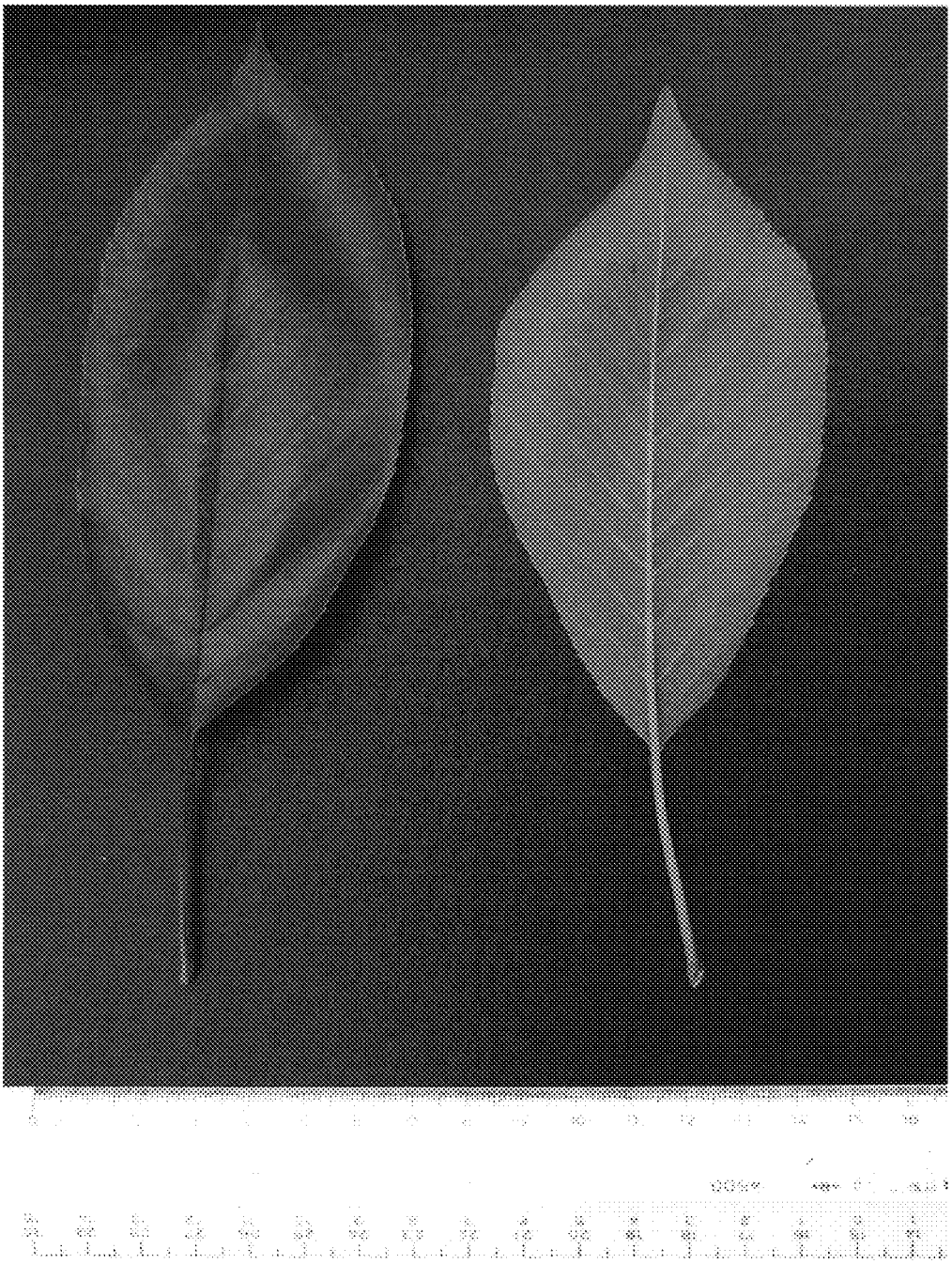
FIG. 3 shows the leaf of 'PA7UNIBO'.
Figure 4:
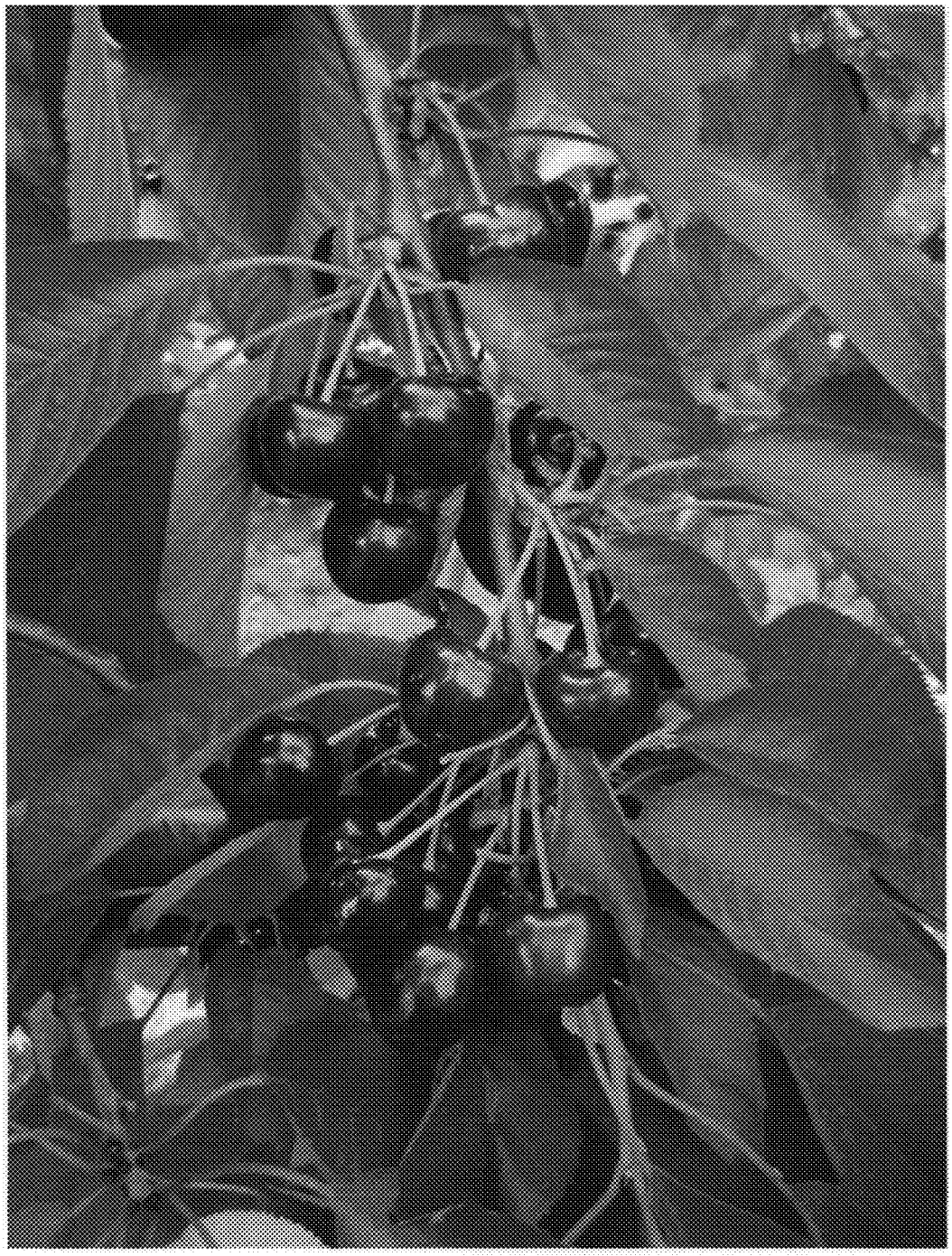
FIG. 4 shows fruits of 'PA7UNIBO'.
Figure 5:
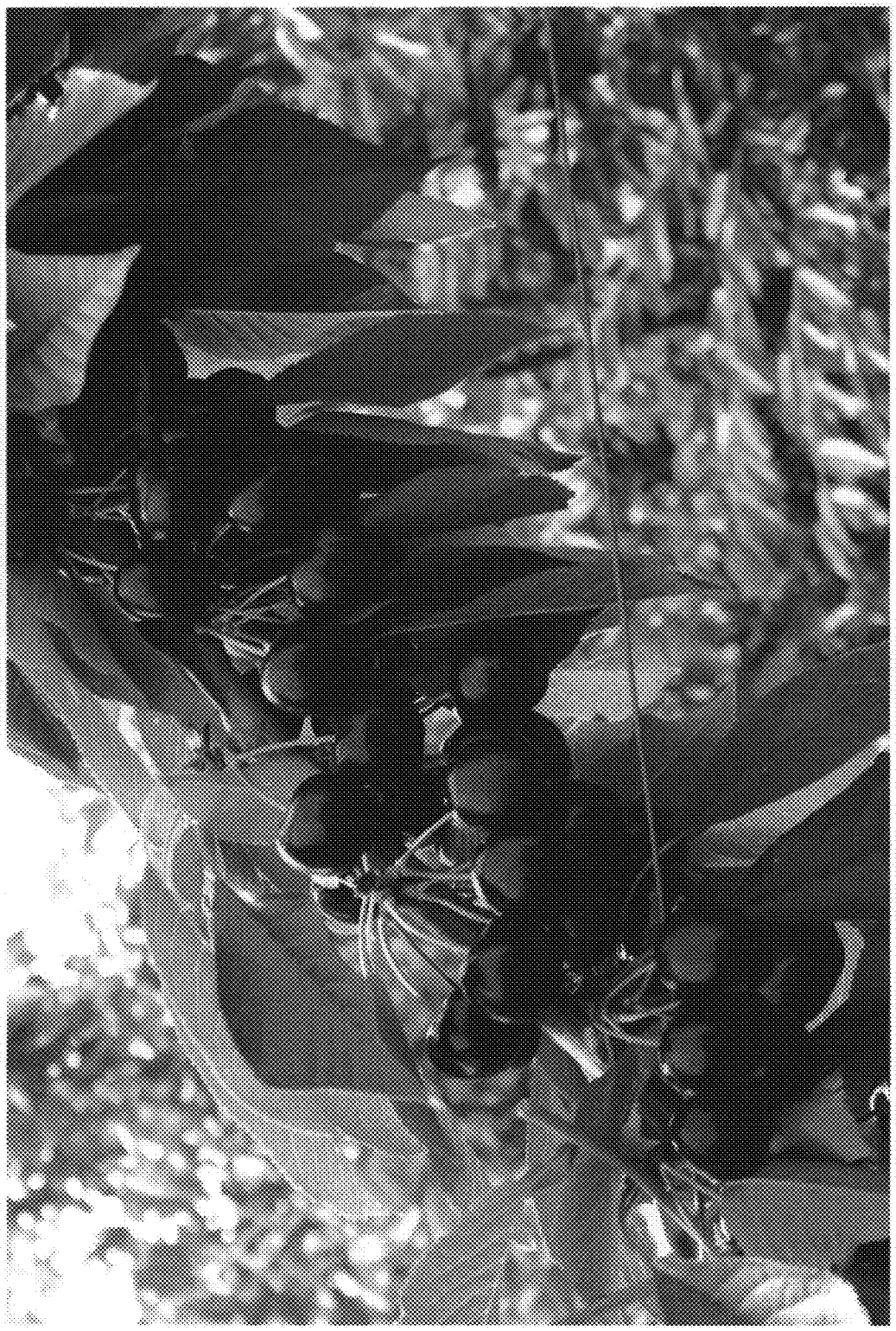
FIG. 5 shows fruits of 'PA7UNIBO'.

General:
- *Age of described tree(s)*.—5 years slender spindle training system.
- *Location of described trees(s)*.—Vignola, Modena Province, Italy.
- *Name of color chart used*.—Royal Horticultural Society Colour Chart.
- *Name of root stock*.—'Gisela 6'.

Tree:
- *Vigor*.—High.
- *Height*.—4.5 meters.
- *Spread*.—3 meters.
- *Growth habit*.—Open.
- *Canopy density*.—Medium.
- *Trunk diameter at specified height*.—19-22 cm, as measured at about 5 cm above graft joint.
- *Trunk color*.—Gray (201A).
- *Bark texture*.—Medium rough.
- *Tendency toward alternate bearing*.—No.
- *Winter hardiness*.—Unknown; no winter cold damage found in this Po Valley district.
- *Chilling requirement*.—Unknown.
- *Fruit production*.—Produces regularly at about 12-15 ton/ha in Vignola area.

Branch:
- *Length*.—150-200 cm.
- *Diameter*.—3-4 cm.
- *Crotch angle*.—45°-60° depending on training system.
- *Bark color*.—Reddish-brown (183B) with gray (201A).
- *Bark texture*.—Medium rough.

Current year shoot:
- *Length*.—50-60 cm.
- *Color*.—Reddish-brown (200C) with fairly widespread gray overtone (201A).
- *Diameter*.—6-12 mm.
- *Texture*.—Lightly rough.

Winter hardiness:
- *USDA hardiness zone*.—Unknown.
- *Chilling requirement*.—Unknown.

Flower buds:
- *Number per spur*.—5-6, but usually 6.
- *Shape*.—Sub-globose.
- *Length*.—About 1 cm.
- *Diameter*.—Under 1 cm.
- *Color*.—Reddish purple (187C).

Flowers:
- *Number per cluster*.—Minimum 18, maximum 20 per spur; 3-4 per bud. Bloom is abundant.
- *Relative position of petals*.—Petals overlap slightly.
- *Diameter*.—30-35 mm.
- *Depth*.—10-15 mm, measured as distance from receptacle to maximum petal aperture.
- *Is pollen produced*?.—Yes.
- *Coloration of pollen*.—Pale yellow (12A).
- *Amount of pollen*.—Abundant.

Sepal:
- *Length*.—5-6 mm.
- *Shape*.—Pointed.
- *Width*.—3-4 mm.
- *Apex*.—Pointed.
- *Base*.—Flat.
- *Margin descriptors*.—Circular.
- *Color*.—Upper surface. — Pale green 142B.
- *Color*.—Lower surface. — Pale green 142A with red (173A).
- *Texture*.—Light pubescence on both surfaces.

Petal:
- *Number per flower*.—5.
- *Shape*.—Circular.
- *Length*.—18-20 mm.
- *Width*.—16-18 mm.
- *Apex*.—Slightly sunken.
- *Base*.—Slightly pointed.
- *Margin*.—Repand.
- *Color*.—Upper surface. — White 20D.
- *Color*.—Lower surface. — White 20D.
- *Texture*.—Both superior and inferior pages of the petals are smooth.

Bloom:
- *Date of bud burst*.—7-8 Apr. 2013.
- *Date of first bloom*.—13 Apr. 2013.
- *Date of full bloom*.—16 Apr. 2013.
- *Date of last bloom*.—21 Apr. 2013.

Pedicel:
- *Length*.—28-35 mm.
- *Diameter*.—About 1.2 mm.
- *Color*.—Pale green 144A.

Pistil:
- *Quantity*.—1.
- *Size*.—19-21 mm.
- *Color*.—Pale green 144D.

Anthers:
- *Quantity*.—28-30, with about 70% of 10-13 mm in length, positioned slightly below the top of the stigma, and the remaining 30% varying from 5-8 mm. White filament (20D).
- *Size*.—About 1 mm diameter.
- *Color*.—Orange-yellow 15C.

Stigma:
- *Quantity*.—1.
- *Size*.—1.0-1.2 mm diameter.
- *Color*.—Yellow-green (144B).

Styles:
- *Quantity*.—1.
- *Size*.—14-16 mm length.
- *Color*.—Yellow-green (144B).

Ovary:
- *Quantity*.—1.
- *Size*.—3-4 mm.
- *Color*.—Pale green 144A.

Leaves:
- *Length*.—12.2-14.1 mm.
- *Width*.—6.5-6.9 mm.

*Shape*.—Lanceolate-elliptical.
*Apex shape*.—Pointed.
*Base shape*.—Pointed.
*Margin*.—Fine toothed.
*Color*.—Upper surface. — Dark green 137 B.
*Color*.—Lower surface. — Pale green 147B veined green-yellow (152A) in center.
*Texture*.—The superior page of the leaf is smooth, whereas the inferior page of the leaf is lightly rough.
*Glands*.—The nectaries are present generally in a number of two for each leaf, they are renifrom, with length 2-3 mm, width 1-2 mm, and reddish in color (183A).

Petiole:
*Length*.—4.5-5 cm.
*Diameter*.—About 2 mm.
*Color*.—Pale green lower 144A and reddish upper (183A).

Fruit:
*Shape*.—Depressed heart-shaped.
*Diameter*.—Mostly 30 mm.
*Height*.—24-27 mm.
*Weight*.—12-13 grams on average.
*Number per cluster*.—5-10 per spur.
*Skin color* (*include ground color and over color*).—Shiny dark red (187B) tending to blackish-dark red (187A) at advanced maturity.
*Presence of lenticels*.—Yes.
*Density of lenticels*.—Medium-high.
*Skin thickness*.—Medium-thin.
*Skin texture*.—Smooth.
*Anthocyanin coloration present near skin*?.—No.
*Tenacity of flesh to stone*.—Low.
*Flesh color*.—Red (53A).
*Flesh texture*.—Fine.
*Juiciness*.—High.
*Juice analysis* (*brix, acidity, tss, etc*.).—21.9 Brix and 11.8 g/l malic acid (2012-2015 data).
*Stone size*.—The weight average of the stone is 0.45 gram, the height ranges from 0.9 to 1.3 cm, and the diameter ranges from 0.8 to 1.0 cm.
*Stone shape*.—Shape of stone in ventral view is elliptic, apex is pointed, base is circular, semi-cling.
*Stone color*.—Pale brown (165D).
*Use*.—Fresh market.

Kernel:
*Shape*.—Ovate.
*Height*.—Ranges from 0.6 to 1.0 cm.
*Width*.—Ranges from 0.5 to 0.8 cm.
*Thickness*.—Ranges from 0.2 to 0.4 mm.

Fruit stem:
*Length*.—35-38 mm.
*Diameter*.—Just over 1 mm.
*Color*.—Green (143A).

Harvest:
*Maturity date range*.—June 10-June 25, approximately 26 days after 'Burlat' and about 6 to 9 days after 'Bing'. Optimum harvest dates of 'PA7UNIBO' in Modena Province are June 15-20.
*Harvest date range* (*if different*).—Same as above. The diploid cultivar 'PA7UNIBO' is self-fertile, with the allelic profile of S3S4. Fruit load and yield is high and constant, particularly in the presence of flying insects (e.g., bees, wasps, hornets, beetles, butterflies, etc.). 'PA7UNIBO' possesses high fruit quality traits that hold steady through subsequent pickings, for at least 10 days. The method of propagation of the variety is represented by budding or grafting. Under observation during planting, growing and harvesting under normal cultural and growing conditions in Modena Province, Italy, 'PA7UNIBO' has been tested against the following viruses: ACLSV, ApMV, PRNSV, PDV, CLRV, RpRSV, CNRMV, PPV, TBSV, LChV-1, LChV-1, SLRSV, ArMV, APLPV. The results were negative, i.e., 'PA7UNIBO' was free from the above-mentioned viruses. Because of the outstanding and unique horticultural characters of the claimed plant, especially its long harvest period and large size, this cherry can be planted to extend the cultivar's season. Although this new variety of cherry possesses the above-described characteristics, it is to be understood that variations and fluctuations may occur in the magnitude and qualities due to changes in growing and climate conditions, irrigation, fertilization, pruning and pest control.

What is claimed:

1. A new and distinct cherry tree, as herein described and illustrated.

* * * * *